(12) United States Patent
Murray

(10) Patent No.: US 6,749,811 B2
(45) Date of Patent: Jun. 15, 2004

(54) MOLECULARLY IMPRINTED POLYMER SOLUTION ANION SENSOR

(75) Inventor: George M. Murray, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/272,834

(22) Filed: Oct. 16, 2002

(65) Prior Publication Data

US 2003/0129092 A1 Jul. 10, 2003

Related U.S. Application Data

(63) Continuation-in-part of application No. 09/300,867, filed on Apr. 28, 1999, now abandoned.
(60) Provisional application No. 60/083,365, filed on Apr. 28, 1998, and provisional application No. 60/329,652, filed on Oct. 16, 2001.

(51) Int. Cl.[7] .................. G01N 7/00; G01N 17/00; G01N 21/00; G01N 21/75; G12B 13/00
(52) U.S. Cl. ................. 422/91; 422/68.1; 422/50; 422/52; 422/55; 422/83; 422/88; 422/82.05; 422/82.07; 422/82.08; 436/43; 436/164; 436/166; 436/172; 73/1.01; 73/1.02; 73/23.2; 73/53.01
(58) Field of Search .................. 422/91, 88, 82.05, 422/82.07, 82.08, 50, 52, 55, 68.1, 83; 436/43, 164, 166, 172; 73/1.01, 1.02, 23.2, 53.01

(56) References Cited

U.S. PATENT DOCUMENTS

| | | | |
|---|---|---|---|
| 4,259,313 A | 3/1981 | Frank et al. | 424/8 |
| 4,283,382 A | 8/1981 | Frank et al. | 424/8 |
| 4,560,248 A | 12/1985 | Cramp et al. | 350/96.34 |
| 4,719,182 A | 1/1988 | Burdick et al. | 436/501 |
| 4,861,727 A | 8/1989 | Hauenstein et al. | 436/136 |
| 5,026,139 A * | 6/1991 | Klainer et al. | 356/128 |
| 5,409,666 A | 4/1995 | Nagel et al. | 422/82.07 |
| 5,498,549 A | 3/1996 | Nagel et al. | 436/172 |
| 5,581,398 A * | 12/1996 | Van Veggel et al. | 359/342 |
| 5,587,273 A * | 12/1996 | Yan et al. | 430/269 |
| 5,639,615 A * | 6/1997 | Selvin et al. | 435/6 |
| 5,846,753 A * | 12/1998 | Akkara et al. | 435/18 |
| 5,854,008 A * | 12/1998 | Diamandis | 435/7.91 |
| 6,316,268 B1 * | 11/2001 | Yang et al. | 436/106 |
| 6,327,410 B1 | 12/2001 | Walt et al. | 385/115 |
| 6,399,397 B1 | 6/2002 | Zarling et al. | 436/518 |
| 6,406,297 B1 | 6/2002 | Raymond et al. | 434/15 |
| 6,409,909 B1 | 6/2002 | Spichiger-Keller et al. | 205/777.5 |

OTHER PUBLICATIONS

Murray et al. (1997). Johns Hopkins APL Technical Digest, vol. 18, No. 4, pp. 464–472.*
Jenkins et al. (1996). Analytical Chemistry, vol. 68, No. 17, pp. 2974–2980.*

* cited by examiner

Primary Examiner—Jill Warden
Assistant Examiner—Brian Sines
(74) Attorney, Agent, or Firm—Francis A. Cooch

(57) ABSTRACT

Devices for measuring and detecting a wide variety of analytes, including polyatomic anions, such as organophosphorus pesticides and nerve agents are provided. The devices function by selectively binding an analyte to a luminescent functionality-imprinted copolymer. The copolymers possess a securely bound luminescent lanthanide ion, such as $Eu^{3+}$, in a coordination complex that has been imprinted to bind the chemical functionality. Also provided are methods for producing the lanthanide-containing molecularly imprinted polymers of the invention.

16 Claims, 9 Drawing Sheets

MOLECULARLY IMPRINTED POLYMER SOLUTION ANION SENSOR

CROSS-REFERENCE TO RELATED APPLICATIONS

The present application is a continuation-in-part of U.S. application Ser. No. 09/300,867 (pending), filed with the United States Patent and Trademark Office on Apr. 28, 1999, which in turn claims the benefit of prior filed Provisional Application No. 60/083,365 which was filed with the United States Patent and Trademark Office on Apr. 28, 1998. The present application also claims the benefit of prior filed Provisional Application No. 60/329,652 which was filed with the United States Patent and Trademark Office on Oct. 16, 2001. The entire disclosure of each of the above-referenced applications is incorporated herein by reference.

BACKGROUND OF THE INVENTION

1. Field of the Invention

The present invention relates generally to the use of molecularly imprinted polymers comprising chelated lanthanides in methods and apparatus for detecting the presence of an analyte.

2. Description of the Related Art

Methods and apparatus for the efficient and accurate detection and quantification of analytes, including polyatomic anion analytes, are of particular interest for use in a wide range of applications. For example, such methods and apparatus are useful in the detection, monitoring, and management of environmental pollutants, including organophosphorus-based pesticides. Organophosphorus-based pesticides, including paraoxon, parathion, and diazinon are widely used in the agriculture industry. Because such materials exhibit a relatively high toxicity to many forms of plant and animal life, and also exhibit relatively high solubility in water, organophosphorus-based pesticides pose a clear threat to aquatic life and to our drinking water. Accordingly, it is imperative to be able to accurately monitor the levels of pesticides in industrial waste waters, agricultural runoffs, and other environments to determine compliance with federal and state regulations, and other safety guidelines.

The efficient and accurate detection of water-soluble anions is also of interest in a number of biomedical applications, including applications wherein it is desirable to detect anionic constituents in fluids associated with dialysis. For example, the detection of the build-up of phosphates in the blood is imperative to the treatment and/or control of renal failure and metabolic bone disease which is commonly associated therewith. Decreased renal function causes phosphates to build up in the blood. This increased serum phosphate combines with calcium, thereby lowering the serum calcium level. The fall in serum calcium levels, in turn, stimulates parathyroid hormone production, which dissolves bone in an effort to restore normal calcium levels. The result of lowered active vitamin D levels is impaired bone synthesis. The active form of vitamin D, normally made in the kidneys, assists in absorbing calcium and phosphorus, and promotes bone formation. Accordingly, the inevitable result of untreated chronic renal failure is bone disease. By monitoring the level of phosphates in the blood, renal failure patients may be better able to control the progression of metabolic bone disease.

Other applications for anion sensing include the detection of nitrates, phosphates, and the like in environmental and waste management applications. For example, nitrate run off from agriculture can cause problems for water quality, especially for children, resulting in the "blue baby" syndrome. Detecting dissolved nutrients, i.e. phosphate and nitrate, is a critical need for evaluating environmental pollution.

Applicants have come to appreciate, for many analyte-detecting applications, that the development of small, portable sensor devices which are relatively highly-selective and sensitive to a target analyte, and are capable of monitoring the analyte levels in real-time, is of particular interest. In certain embodiments, applicants have recognized it is further desirous for such portable sensor devices to operate using low-cost light and power sources.

Unfortunately, although a variety of techniques have been studied based on physical, chemical and biological sensing approaches, there are few conventional, low-cost and portable sensors with the capability to do real time monitoring/detecting of analytes. For example, methods for the unambiguous detection and quantitation of specific gaseous species usually involve separate sampling and analysis steps using complex and expensive devices such as gas chromatography with detection by either flame ionization or mass spectrometry. Much of the technology being used, such as gas chromatography-mass spectroscopy (GC-MS) and high performance liquid chromatography (HPLC), are large (not portable), expensive or require sophisticated, often extensive analysis procedures making them undesirable for real-time field analysis.

Furthermore, conventional optical sensors for the detection of aqueous analytes typically rely on small changes in the indices of refraction in response to the presence of an analyte. Commonly used, conventional optical sensors include planar waveguides, optical fibers, metallized prisms, and diffraction gratings. These and other conventional methods typically require extensive analysis procedures that can take up to 24 hours to perform. Although all these techniques have some degree of sensitivity, they lack specificity, rapid detection, real time analysis, easy operation, low cost, and portability.

Recognizing these and other disadvantages and drawbacks associated with conventional sensing methods and apparatus, applicants have developed the present invention.

SUMMARY OF THE INVENTION

The present invention overcomes the aforementioned disadvantages by providing optical sensors that are capable of detecting a variety of analytes, especially polyatomic anionic analytes, with a relatively high degree of selectivity and sensitivity, and also offer the advantages of real time analysis, easy operation, low cost, and portability. Applicants have discovered that molecularly imprinted polymers (MIPs) containing chelated lanthanides can be used to great advantage in optical sensors designed to detect any of a wide range of analytes. In particular, applicants have discovered that the lanthanide-containing MIPs of the present invention exhibit selective binding characteristics for a wide range of target analytes and thus allow for the detection of such target analytes with a relatively high degree of selectivity and sensitivity, and in less time and with fewer false positives than conventional optical sensors. In addition, applicants have discovered that the chelated lanthanides embedded within the present MIPs can be sensitized to absorb excitation energy provided by a low-cost light and power source, such as a light-emitting diode (LED), and to subsequently luminesce to allow for the detection of analytes.

Accordingly, the sensors of the present invention tend to be low-cost, portable, yet highly effective, analyte sensors.

According to one aspect of the present invention, provided are sensor devices for detecting a target analyte. In certain preferred embodiments, the sensor devices of the present invention comprise a molecularly imprinted polymer containing a chelated lanthanide capable of binding the analyte to be detected, and which has operatively associated therewith: a light source for generating excitation energy for the chelated lanthanide of the molecularly imprinted polymer, wherein at least a portion of the excitation energy is absorbed molecularly imprinted polymer; and a detector for detecting luminescent energy generated by the chelated lanthanide upon excitation.

According to another aspect of the present invention, provided are methods of making a molecularly imprinted polymer comprising: mixing a lanthanide salt with one or more polymerizable/lanthanide-coordinating ligand compounds and a polyatomic anion target analyte under conditions effective to produce a chelated lanthanide-analyte complex; co-polymerizing the lanthanide-analyte complex with one or more cross-linking monomers and one or more matrix monomers to form a polymer structure; and removing the polyatomic anion from the polymer structure to form an MIP.

DETAILED DESCRIPTION

The present invention provides optical sensors that employ a molecularly imprinted polymer containing chelated lanthanides, in conjunction with a light source and a detector, to detect a variety of analytes with a relatively high degree of selectivity and sensitivity.

Figure 2:
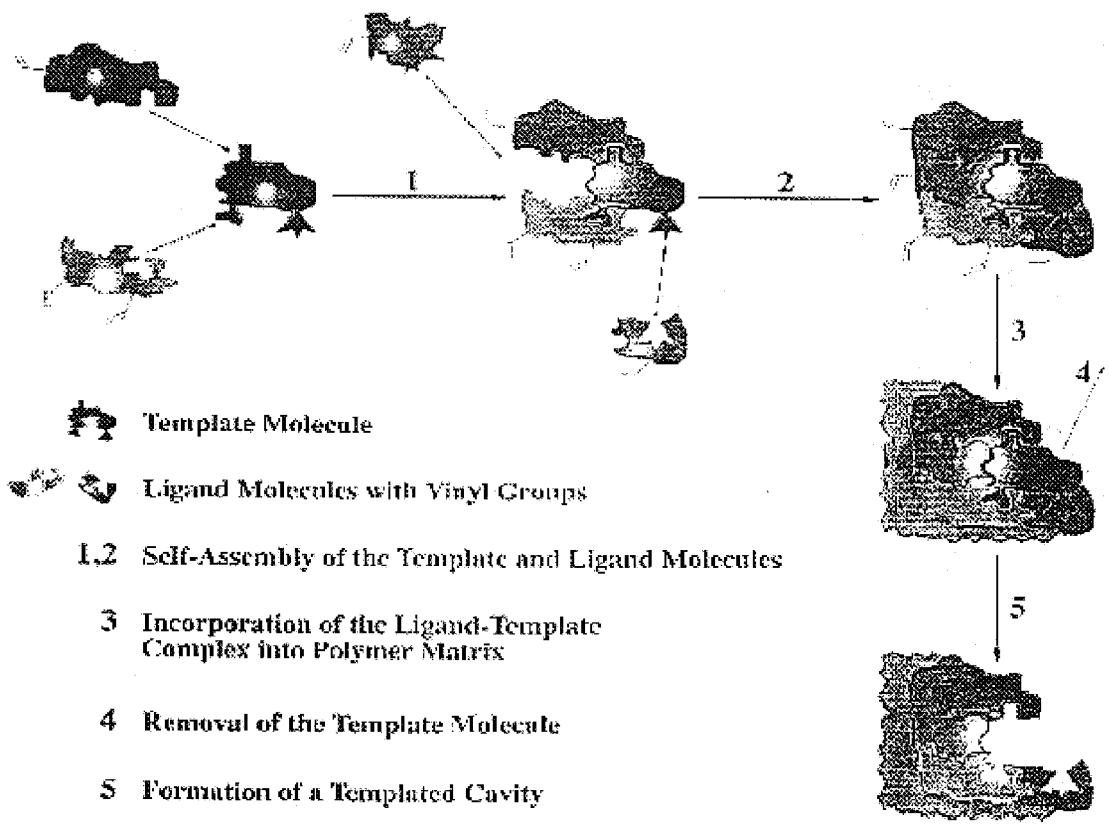
FIG. 2 is a schematic representation of molecular imprinting to obtain a molecularly imprinted polymer according to certain embodiments of the present invention.

As used herein, the term "molecularly imprinted polymer" or "MIP" refers generally to a polymeric mold-like structure having one or more pre-organized recognition sites which complement the shape of at least a portion of a target or imprint molecule and which contain interactive moieties that complement the spacing of, and exhibit an affinity for, at least a portion of the binding sites on the target or imprint molecule. As will be recognized by those of skill in the art, MIPs are typically formed by coordinating imprint molecules with one or more functional monomers to form imprint/monomer complexes (wherein the imprint molecule interacts or bonds with a complementary moiety of the functional monomer via covalent, ionic, hydrophobic, hydrogen-bonding, or other interactions). The monomer/imprint complexes are then polymerized into a highly crosslinked polymer matrix, and the imprint molecules are subsequently dissociated from the functional monomers and removed from the polymer matrix to leave cavities or recognition sites that are relatively shape specific to the imprint molecules and which contain complementary moieties having the ability to rebind chemically with the imprint molecule. FIG. 2 is a schematic representation of one method of molecular imprinting showing self assembly of an imprint to form a imprint complex (1,2); incorporation of the imprint complex into the polymer matrix (3); removal of the imprint molecule; and formation of the imprinted cavity (5).

The combination of the shape specificity of the cavities formed in the MIP and the affinity of the moieties associated with the MIP cavities for the target molecule results in the polymer exhibiting selective binding characteristics for the imprint substance. The terms "selective binding characteristics" and "selective binding interactions" are intended to refer to preferential and reversible binding exhibited by an imprinted polymer for its imprint molecule compared to other non-imprint molecules. Selective binding includes both affinity and specificity of the imprinted polymer for its template molecule.

According to certain embodiments, the MIPs of the present invention comprise lanthanide-containing polymeric structures that exhibit selective binding characteristics towards an analyte to be detected by a sensor device of the present invention (a "target analyte"). Applicants have recognized that such MIPs can be used advantageously as part of an optical sensor device to selectively capture target analyte molecules, by associating such molecules with the MIP lanthanide binding sites, from an analyte solution for detection of the target analyte by the sensor. The present MIPs act not only to provide a site for selectively rebinding the target analyte, but also, act as a source of luminescence, which can be analyzed to determine the amount of target analyte in an analyte solution. The present chelated lanthanides can be sensitized to absorb light energy, including light in the blue region of electromagnetic spectrum, from a variety of light sources, including low-cost LEDs, and to luminesce with an enhanced, detectable intensity. As target analytes are associated with the lanthanides in the present MIPs, the intensity of a certain luminescence line will vary with the amount of anion bound to the polymer (wherein the an amount bound in the MIP is in equilibrium with amount in solution). Such characteristic luminescence can be detected and analyzed to determine the amount of target analyte in solution according to the present invention.

An MIP in accordance with the principles of the present invention can be prepared via any of a wide range of known methods including those described in U.S. Pat. Nos. 5,110,883; 5,321,102; 5,372,719; 5,310,648; 5,208,155; 5,015,576; 4,935,365; 4,960,762; 4,532,232; 4,415,655; and 4,406,792, the entire disclosures of which are incorporated herein by reference. In general, the MIPs of the present invention are formed by: mixing a lanthanide salt with one or more polymerizable ligand compounds and a target analyte under conditions effective to produce a chelated lanthanide-analyte complex; co-polymerizing the lanthanide-analyte complex with one or more cross-linking monomers, and optionally, one or more matrix monomers to form a polymer structure; and removing the imprint molecule from the polymer structure to form an MIP.

As used herein, the term "chelated lanthanide-analyte complex" refers generally to a complex comprising a lanthanide ion having one or more polymerizable ligands associated therewith, wherein the chelated lanthanide is chemically bonded to a target analyte. The term "chemically bonded", as used herein, refers generally to any two moieties that are associated via covalent, ionic, hydrophobic, steric, electrostatic, hydrogen-bonding, or other bonding interactions. According to certain embodiments, suitable chelated lanthanide-analyte complexes can be made according to the present inveniton by mixing stoichiometric amounts of a lanthanide metal salt with one or more complexing ligands in an aqueous solution and evaporating to near dryness. Water or alcohol/water mixtures of the lanthanide metal, ligands, and target analyte in stoichiometric ratios, evaporated to dryness, are preferred to obtain near quantitative yields of the desired chelated lanthanide-analyte complex.

In the present invention, a lanthanide is chosen as the transducer because the lanthanide ions have excellent spectroscopic properties such as long luminescence lifetimes and narrow bandwidths, usually only a few nanometers. Any of a wide range of lanthanide metal salts capable of dissociating in solution to form a lanthanide ion, and combinations of two or more thereof, are suitable for use in the present invention. Examples of suitable lanthanide salts include halides, nitrates, perchlorates, and the like, of lanthanum (La), cerium (Ce), praseodymium (Pr), neodymium (Nd), promethium (Pm), samarium (Sm), europium (Eu), gadolinium (Gd), terbium (Th), dysprosium (Dy), holmium (Ho), erbium (Er), thulium (Tm), ytterbium (Yb), and lutetium (Lu). Preferred lanthanide salts of lanthanide ions that exhibit a narrow-line luminescence including salts of the +3 ions of samarium, europium, dysprosium, terbium, and neodymium. In especially preferred embodiments, the lanthanide salts are salts of the +3 ions of europium and terbium.

Any suitable complexing ligand compounds capable of coordinating with a lanthanide of the present invention and being capable of being polymerized with one or more other polymerizable monomers while chelated to the lanthanide can be used in the present invention. Examples of suitable complexing ligand monomers include a wide range of mono- and bi-dentate ligands including nitrogen-, hydroxyl-, acid-, and/or ester-containing organic compounds such as: beta-diketones, including, vinyldibenzoylmethane, divinyldibenzoylmethane, and the like; phenanthrolines, including vinyl-substituted 1,10-phenanthroline, and the like; mono-, di-, and tri-acids and esters, including 4-vinyl benzoic acid, methyl-3,5-divinyl benzoate, and the like; oximes, including 4-vinyl-2-hydroxybenzaldehyde oxime (vinylsalicylaldoxime), and the like; 2-hydroxy-1,2-di-4-vinylphenylethanone (benzoin oxime vinyl derivative), and the like; polyaminopolycarboxylic acids including EDTA, and the like; (poly)pyridines; calixarenes; mixtures of two or more thereof; and the like. Other examples of suitable ligand monomers for use in the present invention include those described in Jenkins, A., et al., "Ultratrace Determination of Selected Lanthanides by Luminescence Enhancement," *Anal. Chem.*, 68(17) :2974–2980 (1996)(the entire disclosure of which is incorporated herein by reference). Certain preferred complexing ligand compounds include vinyldibenzoylmethane, divinyldibenzoylmethane, vinyl-substituted 1,10-phenanthroline, 4-vinyl benzoic acid, methyl-3,5-divinyl benzoate, 4-vinyl-2-hydroxybenzaldehyde oxime, 2-hydroxy-1,2-di-4-vinylphenylethanone (benzoin oxime vinyl derivative), and mixtures of two or more thereof.

Figure 3:
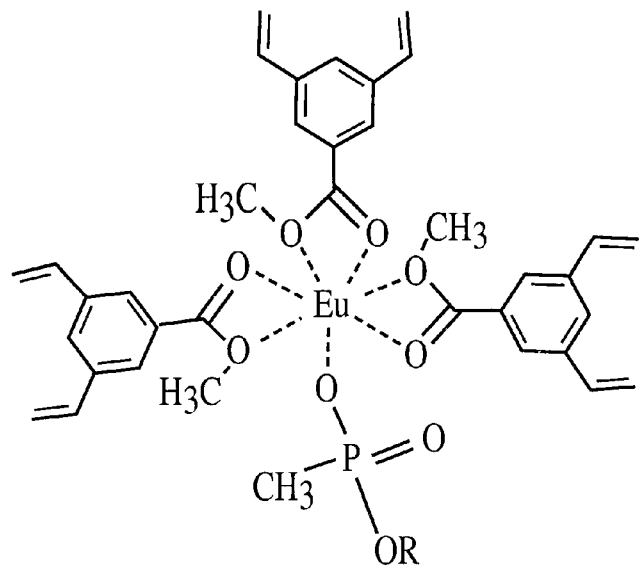
FIG. 3 depicts the structural representation of an exemplary chelated lanthanide-analyte complex according to certain embodiments of the present invention.

The particular combination of complexing ligands and relative amounts thereof used for any given application of the present invention may vary depending on a number of factors including, the lanthanide ion to be used, the target analyte (in particular the anionic charge associated therewith, if any) to be bound thereto, and the light source to be used in the sensor device. As described above, the chelated lanthanide monomer suitable for any particular application according to the present invention should have a charge which complements the charge (if any) on the target analyte such that the chelated lanthanide is capable of bonding with the target analyte. In particular, it is desirable that the lanthanide monomer and target analyte form a bond that will resist dissociation during the polymerization process, but will subsequently release the target analyte to leave behind a suitable set of chelated lanthanide binding sites when the target analyte is removed. For example, in certain embodiments wherein the lanthanide ion is europium 3+ and the target analyte is a polyatomic anion, including organophosphorus anions, it is preferred to use about 3 moles of ligands selected from the group consisting of 4-vinyl benzoic acid, methyl-3,5-divinyl benzoate, 4-vinyl-2-hydroxybenzaldehyde oxime, 2-hydroxy-1,2-di-4-vinylphenylethanone (benzoin oxime vinyl derivative), vinyldibenzoylmethane, divinyldibenzoylmethane, vinyl-substituted 1,10-phenanthroline and mixtures of two or more thereof, to one mole of europium ion and one mole of target analyte. FIG. 3 shows an example of such a chelated lanthanide-analyte complex.

Figure 4:
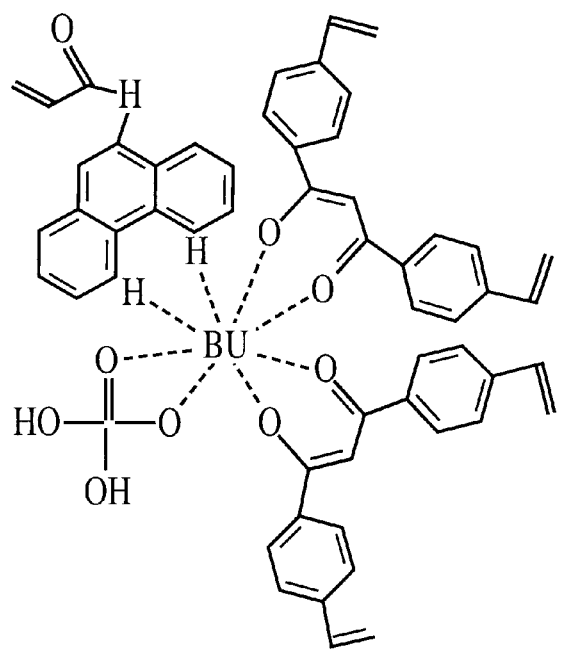
FIG. 4 depicts the structural representation of an exemplary chelated lanthanide-analyte complex according to certain other embodiments of the present invention.

In addition, in preferred embodiments, the complexing ligands are selected to enhance the luminescence intensity of the lanthanide. It is particularly desirable, in certain preferred embodiments, to sensitize the lanthanide such that, when the chelated lanthanide is incorporated in an MIP, a low-cost light source, such as an LED, and be used to cause the lanthanide to luminesce, and in turn, provide a means of target analyte analysis with low limits of detection. As will be recognized, it is desirable for the selected ligands to overlap the triplet state of the lanthanide. For example, in certain preferred embodiments wherein the lanthanide ion is europium 3+ and the target analyte is a polyatomic anion, including organophosphates, nitrate, perchlorate, and the like, it is preferred to use about 3 moles of ligands selected from the group consisting of vinyldibenzoylmethane, divinyldibenzoylmethane, vinyl-substituted 1,10-phenanthroline, and mixtures of two or more thereof, to one mole of europium ion and one mole of target analyte. FIG. 4 shows an example of such a preferred chelated lanthanide-analyte complex.

In light of the disclosure herein, those of skill in the art will be readily able to produce chelated lanthanide-analyte complexes suitable for use in a wide range of applications according to the present invention without undue experimentation.

According to certain embodiments of the present invention, the polymerization step comprises co-polymerizing a chelated lanthanide-analyte complex with one or more cross-linking monomers, and optionally, one or more additional matrix monomers to form a polymer structure. Any of a wide range of crosslinking monomers can be used according to the present invention. Suitable crosslinking monomers/agents that lend rigidity to the MIP are known to those skilled in the art, and include di-, tri- and tetrafunctional acrylates or methacrylates, divinylbenzene (DVB), alkylene glycol and polyalkylene glycol diacrylates and methacrylates, including ethylene glycol dimethacrylate (EGDMA) and ethylene glycol diacrylate, vinyl or allyl acrylates or methacrylates, divinylbenzene, diallyldiglycol dicarbonate, diallyl maleate, diallyl fumarate, diallyl itaconate, vinyl esters such as divinyl oxalate, divinyl malohate, diallyl succinate, triallyl isocyanurate, the dimethacrylates or diacrylates of bis-phenol A or ethoxylated bis-phenol A, methylene or polymethylene bisacrylamide or bismethacrylamide, including hexamethylene bisacrylamide or hexamethylene bismethacrylamide, di(alkene) tertiary amines, trimethylol propane triacrylate, pentaerythritol tetraacrylate, divinyl ether, divinyl sulfone, diallyl phthalate, triallyl melamine, 2-isocyanatoethyl methacrylate, 2-isocyanatoethylacrylate, 3-isocyanatopropylacrylate, 1-methy:L-2-isocyanatoethyl methacrylate, 1,1-dimethyl-2 isocyanaotoethyl acrylate, tetraethylene glycol diacrylate, tetraethylene glycol dimethacrylate, triethylene glycol diacrylate, triethylene glycol dimethacrylate, hexanediol dimethacrylate, hexanediol diacrylate, and the like.

Any suitable monomer that provides an accurate imprint of the imprint molecule upon polymerization may be optionally used in addition to the crosslinking monomers and chelated lanthanide-analyte complexes to synthesize a MIP in accordance with the principles of the present invention. Examples of suitable monomers include any of the complexing ligand monomers described above for forming a chelated lanthanide-analyte complex. Further suitable non-limiting examples of monomers that can be used for preparing a MIP of the present invention include: methylmethacrylate, other alkyl methacrylates, alkylacrylates, allyl or aryl acrylates and methacrylates, cyanoacrylate, styrene, alpha-methyl styrene, vinyl esters, including vinyl acetate, vinyl chloride, methyl vinyl ketone, vinylidene chloride, acrylamide, methacrylamide, acrylonitrile, methacrylonitrile, 2-acetamido acrylic acid; 2-(acetoxyacetoxy)ethyl methacrylate 1-acetoxy-1,3-butadiene; 2-acetoxy-3-butenenitrile; 4-acetoxystyrene; acrolein; acrolein diethyl acetal; acrolein dimethyl acetal; acrylamide; 2-acrylamidoglycolic acid; 2-acrylamido-2-methyl propane sulfonic acid; acrylic acid; acrylic anhydride; acrylonitrile; acryloyl chloride; (R)-alpha-acryloxy-beta, beta'-dimethyl-g-butyrolactone; N-acryloxy succinimide N-acryloxytris(hydroxymethyl) aminomethane; N-acryloyl chloride; N-acryloyl pyrrolidinone; N-acryloyltris(hydroxymethyl)amino methane; 2-amino ethyl methacrylate; N-(3 aminopropyl)methacrylamide; (o, m, or p)-amino-styrene; t-amyl methacrylate; 2-(1 aziridinyl)ethyl methacrylate; 2,2'-azobis-(2-amidinopropane); 2,2'-azobisisobutyronitrile; 4,4'-azobis-(4-cyanovaleric acid); 1,1'-azobis-(cyclohexanecarbonitrile); 2,2'-azobis-(2,4 dimethylvaleronitrile); 4-benzyloxy-3-methoxystyrene; 2-bromoacrylic acid; 4-bromo-1-butene; 3-bromo-3,3-difluoropropane; 6-bromo-1-hexene; 3-bromo-2-methacrylonitrile; 2-(bromomethyl)acrylic acid; 8-bromo-1-octene; 5-bromo-1-pentene; cis-1-bromo-1-propene; beta-bromostyrene; p-bromostyrene; bromotrifluoro ethylene; (t)-3-buten-2-ol; 1,3-butadiene; 1,3-butadiene-1,4-dicarboxylic acid; 3-butenal diethyl acetal; 1-butene; 3 buten-2-ol; 3-butenyl chloroformate; 2-butylacrolein; N-t-butylacrylamide; butyl acrylate; butyl methacrylate; (o,m, p)-bromostyrene; t-butyl acrylate; (R)-carvone; (S)-carvone; (-)-carvyl acetate; cis-3-chloroacrylic acid; 2-chloroacrylonitrile; 2-chloroethyl vinyl ether; 2 chloromethyl-3-trimethylsilyl-1-propene; 3-chloro-1-butene; 3-chloro-2-chloromethyl-1 propene; 3-chloro-2-methyl propene; 2,2-bis(4-chlorophenyl)-1,1-dichloroethylene; 3 chloro-1-phenyl-1-propene; m-chlorostyrene; o-chlorostyrene; p-chlorostyrene; 1 cyanovinyl acetate; 1-cyclopropyl-1-(trimethylsiloxy) ethylene; 2,3-dichloro-1-propene; 2,6-dichlorostyrene; 1,3-dichloropropene; 2,4-diethyl-2,6-heptadienal; 1,9-decadiene; 1-decene; 1,2-dibromoethylene; 1,1-dichloro-2, 2-difluoroethylene; 1,1-dichloropropene; 2,6 difluorostyrene; dihydrocarveol; (±)-dihydrocarvone; (-)-dihydrocarvyl acetate; 3,3 dimethylacrylaldehyde; N,N'-dimethylacrylamide; 3,3-dimethylacrylic acid; 3,3 dimethylacryloyl chloride; 2,3-dimethyl-1-butene; 3,3-dimethyl-1-butene; 2-dimethyl aminoethyl methacrylate; 2,4-dimethyl-2,6-heptadien-1-ol; 2,4-dimethyl-2,6-heptadienal; 2,5-dimethyl-1,5-hexadiene; 2,4-dimethyl-1,3-pentadiene; 2,2-dimethyl-4-pentenal; 2,4-dimethylstyrene; 2,5-dimethylstryene; 3,4-dimethylstryene; divinyl benzene; 1,3 divinyltetramethyl disiloxane; 8,13-divinyl-3,7,12,17-tetramethyl-21H,23H-porphine; 8,13-divinyl-3,7,12,17-tetramethyl-21H,23H-propionic acid; 8,13-divinyl-3,7,12, 17 tetramethyl-21H,23H-propionic acid di-sodium salt; 3,9-divinyl-2,4,8,10 tetraoraspiro[5,5]undecane; divinyl tin dichloride; 1-dodecene; 3,4-epoxy-1-butene; 2-ethyl acrolein; ethyl acrylate; 2-ethyl-1-butene; (±)-2-ethylhexyl acrylate; (±)-2-ethylhexyl methacrylate; 2-ethyl-2-(hydroxymethyl)-1,3-propanediol triacrylate; 2-ethyl (hydroxymethyl)-1,3-propanediol trimethacrylate; ethyl methacrylate; ethyl vinyl ether; ethyl vinyl ketone; ethyl vinyl sulfone; (1-ethylvinyl)tributyl tin; m-fluorostyrene; o fluorostyrene; p-fluorostyrene; glycol methacrylate (hydroxyethyl methacrylate); GA GMA; 1,6-heptadiene; 1,6-heptadienoic acid; 1,6-heptadien-4-ol; 1-heptene; 1-hexen-3-ol; 1-hexene; hexafluoropropene; 1,6-hexanediol diacrylate; 1-hexadecene; 1,5-hexadien-3,4 diol; 1,4-hexadiene; 1,5-hexadien-3-ol; 1,3,5-hexatriene; 5-hexen-1, 2-diol; 5-hexen-1-ol; hydroxypropyl acrylate; 3-hydroxy-3, 7,11-trimethyl-1,6,10-dodecatriene; isoamyl methacrylate; isobutyl methacrylate; isoprene; 2-isopropenylaniline; isopropenyl chloroformate; 4,4'-isopropylidene dimethacrylate; 3-isopropyl-a-a-dimethylbenzene isocyanate; isopulegol; itaconic acid; itaconalyl chloride; lead (11) acrylate; (t)-:linalool; linalyl acetate; p-mentha-1,8-diene; p-mentha-6,8-dien-2-ol; methyleneamino acetonitrile; methacrolein; [3-(methacryloylamino)-propyl]trimethylammonium chloride; methacrylamide; methacrylic acid; methacrylic anhydride; methacrylonitrile; methacryloyl chloride; 2-(methacryloyloxy)ethyl acetoacetate; (3-methacryloxypropyl)trimethoxy silane; 2-(methacryloxy) ethyl trimethyl ammonium methylsulfate; 2-methoxy propene (isopropenyl methyl ether); methyl-2-(bromomethyl) acrylate; 5-methyl-5-hexen-2-one; methyl methacrylate; N,N'-methylene bisacrylamide; 2-methylene glutaronitrite; 2-methylene-1,3-propanediol; 3-methyl-1,2-butadiene; 2-methyl-1-butene; 3-methyl-1-butene; 3-methyl-1-buten-1-ol; 2-methyl-1-buten-3-yne; 2-methyl-1,5-heptadiene; 2methyl-1-heptene; 2-methyl-1-hexene; 3-methyl-1,3-pentadiene; 2-methyl-1,4-pentadiene; (±)-3-methyl-1-pentene; (±)-4-methyl-1-pentene; (±)-3-methyl-1-penten-3-ol; 2-methyl-1-pentene; alpha-methyl styrene; t-a-methylstyrene; t-beta-methylstyrene; 3-methylstyrene; methyl vinyl ether; methyl vinyl ketone; methyl-2-vinyloxirane; 4 methylstyrene; methyl vinyl sulfonee;

4-methyl5-vinylthiazole; myrcene; t-beta-nitrostyrene; 3-nitrostyrene; 1-nonadecene; 1,8-nonadiene; 1-octadecene; 1,7-octadiene; 7 octene-1,2-diol; 1-octene; 1-octen-3-ol; 1-pentadecene; 1-pentene; 1-penten-3-ol; t-2,4 pentenoic acid; 1,3-pentadiene; 1,4-pentadiene; 1,4-pentadien-3-ol; 4-penten-1-ol; 4 penten-2-ol; 4-phenyl-1-butene; phenyl vinyl sulfide; phenyl vinyl sulfonate; 2-propene-1 sulfonic acid sodium salt; phenyl vinyl sulfoxide; 1-phenyl-1-(trimethylsiloxy)ethylene; propene; safrole; styrene (vinyl benzene); 4-styrene sulfonic acid sodium salt; styrene sulfonyl chloride; 3-sulfopropyl acrylate potassium salt; 3-sulfopropyl methacrylate sodium salt; tetrachloroethylene; tetracyano ethylene; tetramethyldivinyl siloxane; trans 3chloroacrylic acid; 2-trifluoromethyl propene; 2-(trifluoromethyl)propenoic acid; 2,4,4'trimethyl-1-pentene; 3,5-bis(trifluoromethyl)styrene; 2,3-bis(trimethylsiloxy)-1,3butadiene; 1-undecene; vinyl acetate; vinyl acetic acid; 4-vinyl anisole; 9-vinyl anthracene; vinyl behenate; vinyl benzoate; vinyl benzyl acetate; vinyl benzyl alcohol; 3-vinyl benzyl chloride; 3-(vinyl benzyl)-2-chloroethyl sulfone; 4-(vinyl benzyl)-2-chloroethyl sulfone; N-(p-vinyl benzyl)-N,N'-dimethyl amine; 4-vinyl biphenyl (4-phenyl styrene); vinyl bromide; 2-vinyl butane; vinyl butyl ether; 9-vinyl carbazole; vinyl carbinol; vinyl cetyl ether; vinyl chloroacetate; vinyl chloroformate; vinyl crotanoate; vinyl cyclohexane; 4vinyl-1-cyclohexene; 4-vinylcyclohexene dioxide; vinyl cyclopentene; vinyl dimethylchlorosilane; vinyl dimethylethoxysilane; vinyl diphenylphosphine; vinyl 2-ethyl hexanoate; vinyl 2-ethylhexyl ether; vinyl ether ketone; vinyl ethylene; vinyl ethylene iron tricarbonyl; vinyl ferrocene; vinyl formate; vinyl hexadecyl ether; vinylidene fluoride; Ivinyl imidizole; vinyl iodide; vinyl laurate; vinyl magnesium bromide; vinyl mesitylene; vinyl 2-methoxy ethyl ether; vinyl methyl dichlorosilane; vinyl methyl ether; vinyl methyl ketone; 2-vinyl naphthalene; 5-vinyl-2-norbomene; vinyl pelargonate; vinyl phenyl acetate; vinyl phosphonic acid, bis(2-chloroethyl)ester; vinyl propionate; 4-vinyl pyridine; 2-vinyl pyridine; 1-vinyl-2-pyrrolidinone; 2-vinyl quinoline; 1-vinyl silatrane; vinyl sulfone; vinyl sulfone (divinylsulfone); vinyl sulfonic acid sodium salt; o-vinyl toluene; pvinyl toluene; vinyl triacetoxysilane; vinyl tributyl tin; vinyl trichloride; vinyl trichlorosilane; vinyl trichlorosilane (trichlorovinylsilane); vinyl triethoxysilane; vinyl triethylsilane; vinyl trifluoroacetate; vinyl trimethoxy silane; vinyl trimethyl nonylether; vinyl trimethyl silane; vinyl triphenylphosphonium bromide (triphenyl vinyl phosphonium bromide); vinyl tris-(2-methoxyethoxy)silane; vinyl 2-valerate and the like. Acrylate-terminated or otherwise unsaturated urethanes, carbonates, and epoxies can also be used in the MIP. An example of an unsaturated carbonate is allyl diglycol carbonate (CR-39). Unsaturated epoxies include, but are not limited to, glycidyl acrylate, glycidyl methacrylate, allyl glycidyl ether, and 1,2-epoxy-3-allyl propane.

Preferred examples of matrix monomers include styrene, or styrene derivatives, especially those that can act as an optical antenna.

Any ratio of simple monomers to crosslinking monomers that provides a polymeric structure of appropriate integrity can be used to produce an MIP according to the present invention. In light of the disclosure herein, those skilled in the art will be readily able to select suitable ratios of monomers to provide the desired structural integrity and produce MIPs according to the present invention, without undue experimentation.

Any suitable conditions effective to polymerize the monomers of the present invention to produce an MIP without dissociating the chelated lanthanide-analyte complex may be used. The monomers of the present invention may be polymerized via cationic polymerization, anionic polymerization, free radical polymerization, and the like. In preferred embodiments, free radical polymerization is used.

Any UV or thermal free radical initiator known to those skilled in the art can be used in the preferred free radical polymerization. Examples of UV and thermal initiators include benzoyl peroxide, acetyl peroxide, lauryl peroxide, azobisisobutyronitrile (AIBN), t-butyl peracetate, cumyl peroxide, t-butyl peroxide; t-butyl hydroperoxide, bis (isopropyl)peroxy-dicarbonate, benzoin methyl ether, 2,2'-azobis(2,4-dimethylvaleronitrile), tertiarybutyl peroctoate, phthalic peroxide, diethoxyacetophenone, and tertiarybutyl peroxypivalate, diethoxyacetophenone, I-hydroxycyclohexyl phenyl ketone, 2,2-dimethyoxy-2-phenylacetophenone, and phenothiazine, and diisopropylxanthogen disulfide.

When polymerization is complete, the crosslinked polymer may be washed, cryogenically ground to a uniformly fine powder, and/or extensively eluted with nonpolar solvents to remove any unreacted lanthanide-analyte complex. The steps of grinding and/or freezing in liquid nitrogen may be used to maximize surface area and allow for access by the various reagents and samples. Freezing allows the polymer to become brittle enough to be ground and prevents distortions of the polymer by the heat of friction. Polymers used in the construction of optical sensors may be prepared in situ on the distal end of an optical fiber whose surface is prepared by binding a polymerizable agent on the surface.

After polymerization, the imprint molecule may be removed in a manner that does not adversely affect the imprinted cavity. In embodiments wherein the imprint molecule is covalently bound to the functional monomer, any appropriate method can be used to cleave the covalent bond, although the covalent bond formed should preferably be cleaved under conditions suitable to release the imprint molecule after the MIP is formed, without adversely affecting the selective binding characteristics of the MIP. To accomplish this, acetone or other suitable organic solvent may be used to swell the resultant polymers, allowing greater access to the coordinated metal ions because imprinted resins have a relatively low amount of functionalization and are primarily nonionic matrices. The covalent bond that is cleaved to release the imprint molecule can optionally provide an additional polar or ionic site for design and imprinting of the imprint molecule. In preferred embodiments wherein the target analyte is associated with the lanthanide in a non-covalent manner, the non-covalently bound analyte is simply leached or washed out after polymerization. For example, for organophosphorus compound imprinted resins, subsequent to the removal of unreacted monomer, a 1 N aqueous acidic solution may be mixed into the acetone washes, with increasing aqueous acidic phase in each sequential wash, to remove the imprint molecule from the cavities. In certain preferred embodiments, an acidic solvent having a pH of about 4.5 or less is used. In certain other preferred embodiments, resin mass action is used to replace a target anion with an easily exchangeable anion by immersing the polymer in a solution containing the easily exhangable anion at a suitable pH.

According to certain embodiments, the MIP of the present invention is used in conjunction with a light source and a detector to form an optical sensor device for detecting a target analyte.

As used herein, the term "light" refers to optical radiation, whether ultraviolet, visible or infrared. Suitable non-limiting examples of light sources include an argon laser, blue laser, tunable laser, light emitting diode (LED), combinations of two or more thereof, and the like.

Any of a wide range of suitable detectors can be used according to the present invention. Non-limiting examples of suitable detectors include a spectrophotometer, spectrometer (gas or mass), photomultiplier tube, monochromator equipped with a CCD camera, filters, the naked eye, combinations of two or more thereof, and the like.

Preferably, a sensor device of the present invention is produced by operatively associating at least one light source and at least one detector with an MIP. For the purposes of the present invention, two objects are considered to be "operatively associated" when connected or arranged in a manner such that excitation or luminescent energy produced by one of the objects is capable of being absorbed or detected by the other object. The light source, detector and MIP of the present invention, may be operatively associated in any manner such that excitation energy from the light source is transmitted to the MIP and absorbed by the chelated lanthanide, and the luminescent energy produced by the excited lanthanide is transmitted to, and detected by, the detector. In addition, the components of the present sensor devices may be connected or arranged with or in any suitable medium through which excitation or luminescent energy can be transmitted. Examples of suitable media include air, optical devices, such as films or fibers, and combinations of two or more thereof.

According to certain preferred embodiments, the light source, MIP and detector are associated through optical fibers to provide a fiber optic sensor device. In certain embodiments, the fiber optic sensor device for detecting the presence of at least one analyte in a sample, such as an organophosphorus compound, according to the present invention comprises: at least one optical fiber having a proximal end and a distal end for transmitting light energy, the proximal end being disposed within a probe housing, a molecularly imprinted polymer containing a lanthanide-complex disposed on, or bonded to, the distal end of the optical fiber means, wherein the lanthanide-complex is capable of chemically binding with said analyte, a light source for generating excitation energy, said light source being operatively associated with said optical fiber such that said excitation energy passes through said optical fiber means to said MIP, and detection means operatively associated with said optical fiber means, for detecting luminescent energy generated by said lanthanide complex.

In such preferred embodiments, the device may employ a modulated light emitting diode (LED) for excitation and a small photosensor module for detection, with the output going to a microprocessor controlled grated integrator. In addition, an optical multiplex switch may be incorporated into the design so that many sensors can be coupled to one control system, which will allow monitoring of a large area such as found in a building, subway station, shopping mall, airport, etc.

In use, a target analyte, if present, binds to the lanthanide in the molecularly imprinted polymer causing it to luminesce differently under appropriate excitation. Light from the light source means travels along the optical fiber to its distal end where it undergoes a change caused by interaction with the lanthanide-complex. The modified light returns along the same or another fiber to the detection means which interprets the returned light signal. Detection is based on the change that occurs in the lanthanide's luminescence spectrum when an analyte binds to the lanthanide-complex.

Figure 1:
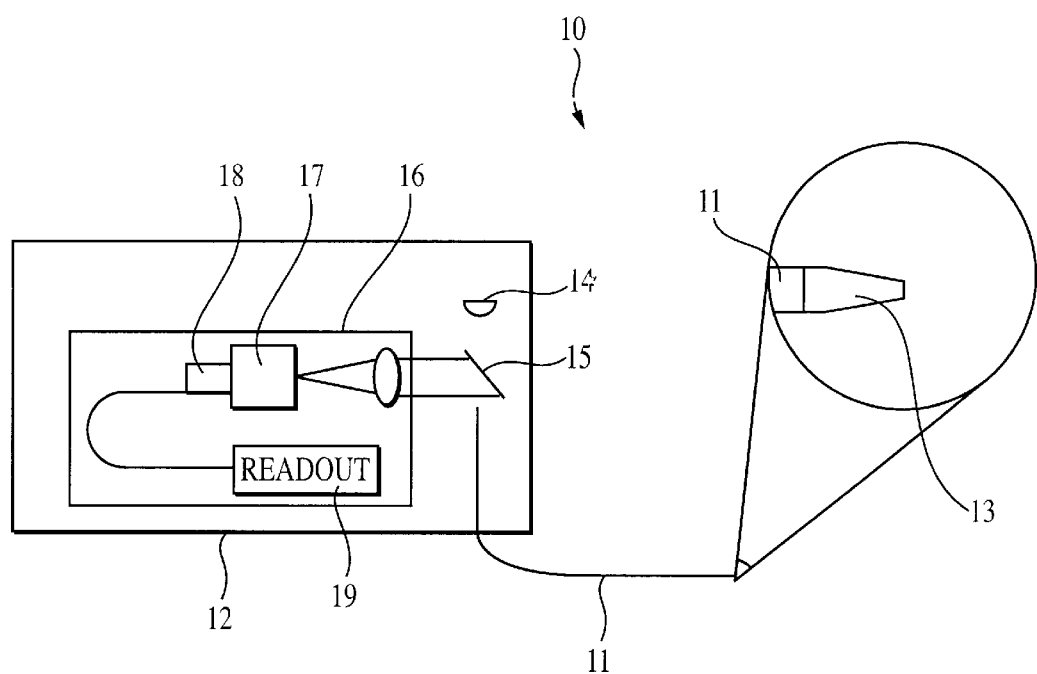
FIG. 1 is a schematic drawing of an optical sensor according to one embodiment of the present invention.

FIG. 1 illustrates an exemplary fiber optic portable sensor device according to certain preferred embodiments of the present invention. The sensor device 10 in FIG. 1 comprises an optical fiber 11 having a proximal end disposed within a sensor housing 12 and a distal end having a molecularly imprinted polymer 13 disposed on (bonded to) the distal end of optical fiber 11. Light source 14 is a blue LED diode from which light in the blue range of the spectrum is emitted. The light is emitted through a dichroic mirror 15 to the proximal end of fiber 11 wherein the light energy is transmitted to the chelated lanthanides in the MIP 13. Any luminescene generated by the lanthanides travels back through fiber 11 and is reflected off the dichroic mirror 15 to detector 16 which comprises a filter 17, a photadiode 18, and a readout 19.

While the exemplary device shown in FIG. 1 comprises a single housing for the detector and light source only, any suitable combination of one or more of the light source, detector, and/or MIP can be housed within one or more device housings according to the present invention.

Figure 5:
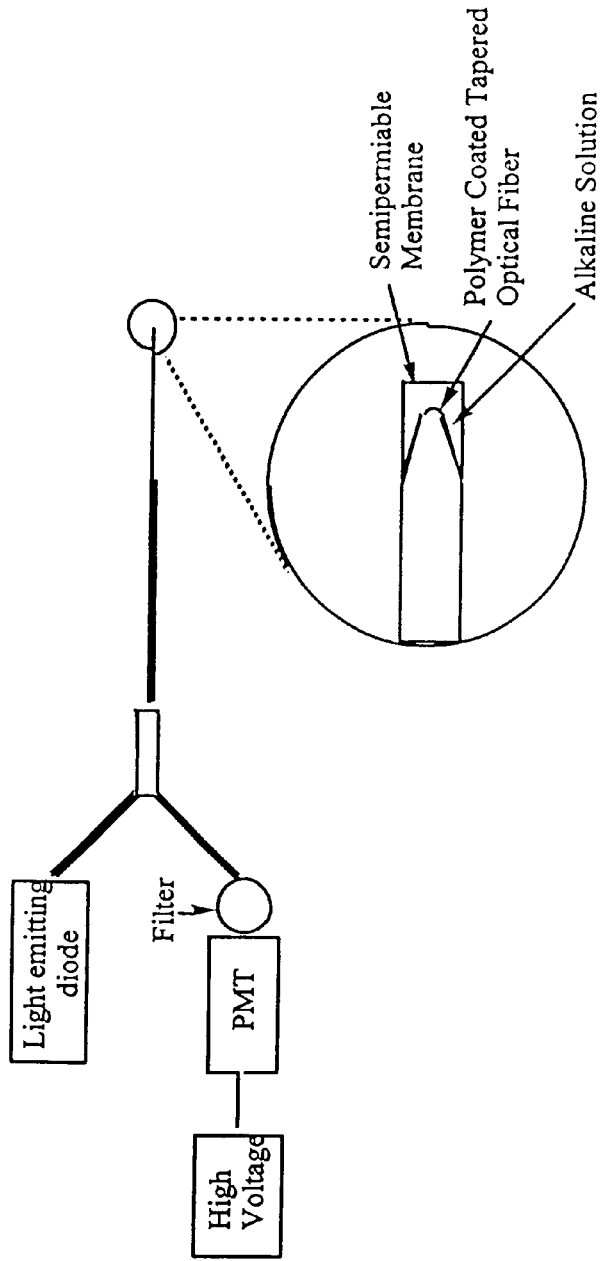
FIG. 5 is a schematic drawing of an optical sensor according to certain preferred embodiments of the present invention.
Figure 6:
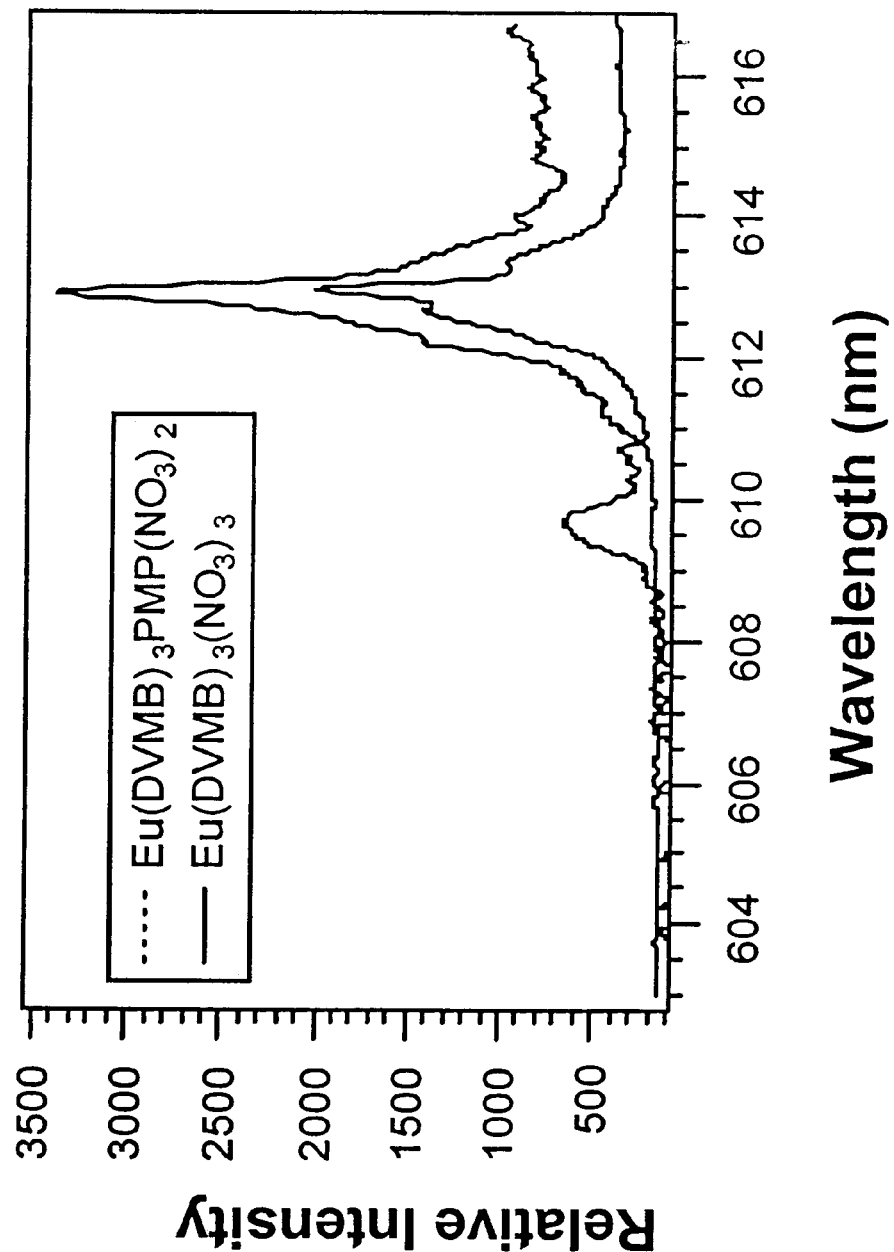
FIG. 6 is laser excited luminescence spectra of $Eu(DMMB)_3(NO_3)_3$ and $Eu(DMMB)_3PMP(NO_3)_2$ crystalline solids excited at 465.8 nm.

In certain embodiments, the distal end (working end) of the sensor may be enclosed within a semi-permeable membrane to separate the analyte-containing media being analyzed from the probe. One function of the membrane is to separate, as far as possible, the analyte (i.e., those components in a sample that can bind to the probe) from interferents (i.e., compounds which may be present but are undesirable because they either interfere with the progress of the desired determination reactions or take part in reactions of their own which compete with those of the component sought and distort or overwhelm the signals that are to be measured). If the sensor probe is configured to detect the hydrolysis products of the nerve agents soman and sarin, then the semi-permeable membrane may be impregnated with an alkaline solution or coated with a nonvolatile alkaline oil, to catalyze the hydrolysis of the nerve agents soman and sarin to their respective hydrolysis products. FIG. 5 illustrates an exemplary sensor according to an embodiment.

The optical sensor devices of the present invention can be used to detect any of a wide variety of analytes. In particular, the present sensors can be used to great advantage in the selective and accurate detection of polyatomic anion analytes. While those of skill in the art will recognize that optical sensors can be designed according to the teachings herein to detect any of a wide range of polyatomic anions, a non-limiting list of exemplary polyatomic anions detectable by the present sensors include: organic polyatomic anions, such as, organophosphates including sarin, soman, tabun, VX, malation, parathion, paraoxon, diazinon, adenizine triphosphate (ATP), hydrolysis products thereof, and the like; nitrate, sulfate, sulfite, selenate, other oxyanions including pertechnitate, molybdate, perchlorate, periodate, hypochlorite, and the like.

EXAMPLES

The present invention will be further illustrated in the following, non-limiting Examples. The Examples, which exemplify a sensor device for detecting benzoates and the hydrolysis products of the nerve gases soman and sarin, are illustrative only and do not limit the claimed invention regarding the materials, conditions, process parameters and the like recited herein.

It should be noted that open air testing of actual chemical agents has been forbidden since the late 1960's when an agent was inadvertently sprayed on desert grazing-land in Utah. Therefore, an exemplary device designed for the detection of agents either cannot easily be tested, or it must be designed to respond to a surrogate material, increasing the possibilities for false alarms. In order to circumvent this problem, the sensor described below was designed to measure the hydrolysis product of soman, pinacolylmethylphosphonate (PMP). This approach allows for the indirect detection of the agents since the agents will rapidly hydrolyze in water. The inclusion of a hydrolyzing surface coating can be used if gas phase sensing is required. This scheme minimizes the hazards and difficulties associated with directly working with these toxic agents. The polymers used in the sensor were imprinted for PMP because since the polymer bound functional end of the molecule is the same for the hydrolysis product of either soman or sarin.

Unless otherwise indicated, the reagent materials were obtained from commercial suppliers and used without further purification. Analytical reagent grade chemicals were used along with deionized water to prepare solutions. PMP and sodium phosphate were obtained from Aldrich (Aldrich, Milwaukee, Wis. 53233). Neat liquid standards of Phosdrin and Dichlorvos as well as solid standards of Methyl Parathion and Dimethoate were obtained from Supelco (Supelco Chromatography Products, Bellefonte, Pa. 16823). Malathion, Thionazin, and Dibutyl Chlorendate were obtained as neat liquid standards from Radian' (Radian International, Austin, Tex. 78720) Luminescence was excited using a model 60X argon ion laser (MWK Industries, Corona, Calif.). Spectra were collected using an f/4, 0.5 m monochromator (Chromex, Albuquerque, N. Mex.) equipped with a Model ST-6 CCD (Santa Barbara Instruments Group, Santa Barbara, Calif.) using Kestrel Spec Software (K&M Co., Torrance, Calif., USA). Spectra were also obtained with an Ocean Optics 52000 Miniature Fiber Optic Spectrometer (Ocean Optics, Dunedin, Fla. 34698) equipped with a 1200 line holographic grating, permanently installed 100 micron slits and a 440 nm cutoff filter.

Molecular absorbance spectra were obtained using a UV/VIS spectrophotometer (Beckman Instruments Inc., Fullerton, Calif., USA). Radiative lifetimes and quantum efficiencies were measured using a Quanta Master Spectrophosphorimeter (Photon Technologies Inc., Ontario, Canada). Electron micrographs were obtained using a Topcon DS-701 dual stage scanning electron microscope (SEM) (Topcon, Paramus, N.J. 07652). Metal concentrations were determined using a Hewlett Packard 4500 Series ICP-MS model G1820A (Hewlett Packard, Wihnington, Del. 19808). Graphs and spectra were plotted and calculations performed using Igor Pro Software (WaveMetrics Inc., Lake Oswego, Oreg. 97035).

Example I

Compound Preparation

Lanthanide complex compounds were synthesized using a stoichiometric ratio of one mole of europium to one mole of PMP and 3 to 7 moles of ligating molecules. (The number of ligating species depended on the number of ligands needed to acquire 9 coordinate Eu3+.) The calculated amount of each ligand was added to the europium solutions. PMP was added to a 50/50 water-methanol mixture to enhance its solubility, then added to the europium/ligand mixture. The resulting solutions were stirred approximately 2 hours, then left to evaporate the solvent. Analogous compounds without PMP were also synthesized. Eu(DVMB)3PMP(NO$_3$)$_2$ and Eu(DVMB)$_3$(NO$_3$)$_3$ were synthesized in the manner detailed above. (Divinyl methyl benzoate (DVMB) was freshly prepared before use since it readily polymerizes.) Shea, K. J., et al., *Macromolecules*, 24:1207–1209 (1991). The stoichiometry of Eu(DVMB) 3PMP(NO$_3$)$_2$ was verified using ICP-MS Eu 16.12% (calculated 16.36%). Low temperature crystal spectra of both compounds were collected from 575 to 700 nm using 465.8 run excitation. Spectra were interpreted to determine the symmetry changes associated with PMT inclusion. Lifetimes and time resolved luminescence spectra of Eu(DVMB)3PMP(NO$_3$)$_2$ and Eu(DVMB)$_3$(NO$_3$)$_3$ were obtained and quantum efficiencies were evaluated with respect to a reference perchlorate solution. Stein, G., et al., *Chem. Phys.*, 62(1):208–213 (1975).

Example 2

Compound Preparation

Lanthanide complex compounds were synthesized using a stoichiometric ratio of one mole of europium to one mole of benzoate anion analyte, namely triethylammonium benzoate (TEAB) or methyl ammonium benzoate (MAB), and about 3 moles of beta-diketone ligating molecules. The benzoate anions were formed by reaction of benzoic acid with a primary and/or a tertiary amine. (The amine's basicity differs by two orders of magnitude, which tunes the reversibility of the analyte interaction with the europium complexes.) Both TEAB and MAB are soluble in organic solvents, which eases the reaction with a hydrophobic tris (beta-diketone) europium complex. MAB and TEAB were reacted with tris(vinyl-benzoylacetonate) europium (TBAE) and tris(1,3-diphenylpropandionate) europium (DPPE) to give four new anionic complexes. The reaction of TEAB with the tris(β-diketonate) europium complexes proceeded instantaneously, while the reaction of MAB with the same complexes were sluggish and needed to be heated to 60° C. for 4 hours to be driven to completion. All four complexes exhibited strong new peaks at ca. 616 nm, which are markedly different from the neutral complexes (three peaks at shorter wavelength). See FIG. 10. Reaction of the trischelate with inorganic phosphate gives a phosphate imprinting complex.

Example 3

Polymer Preparation

Styrenic block copolymers were prepared and the optimal mole percent complex for the preparation of the polymer coating determined. Polymers were prepared by dissolving 1 to 5 mole percent complex compound in 94–98 mole percent styrene. Approximately 1 mole percent of azobisisobutylnitrile (AIBN) was added as an initiator to the mixture described in Example 1. Crosslinked polymers were also prepared using 3 mole percent compound with 1–5 mole percent of a crosslinking agent divinyl benzene (DVB), styrene and AIBN. The resulting solutions were placed in glass vials, purged with nitrogen, and sealed using parafilm and screw on tops. The resulting translucent polymers displayed a slight yellow tint and upon excitation with a uv lamp, displayed the characteristic red-orange luminescence of europium. The best results were obtained from the 3 mole pe overall, had a diminished analyte peak. Polymers with greater than 5 mole percent complex were not used since they tend to become opaque, reducing optical transduction.

The polymers were sonicated for 2–4 hours at 60° C. (Sonication is believed to help maintain homogeneity in the polymer.) Zeng, X.; Murray, G. M. *Separation Science and Technology*, 31:2403–2418 (1996). After sonication, the partially polymerized material was placed in an oven at 60° C. and allowed to cure overnight. The resulting block copolymers were ground to expose a larger surface area of the polymer and facilitate the removal of the imprinting ion. Once ground, the imprint ion is removed in two steps (Id.): (1) swelling in water and gradually increasing amounts of methanol (Helferich, F., *Ion Exchange*, McGraw-Hill: New York, 511(1962)) to remove unreacted monomer and expand the polymer pores, (this produces accessible sites and facilitates the removal of the imprinting ion, and (2) removal of the imprinting ion by acid washing. Acid washing (pH of about 4.5) facilitates the removal of PMP and leaves in its place a weakly coordinated nitrate.

The optimal conditions for swelling the polymer include a series methanol/water washes, followed by washing with a weak nitric acid solution. The spectrum of the washed polymer shows the 610 nn peak was no longer visible, demonstrating that PMP was effectively removed. A small residual peak at 610 nm was viewed in some of the polymers resulting from some hydrolysis product trapped in the deeper levels of the polymer. The overall intensity of the polymer's luminescence also decreases upon washing since the nitrate is only weakly coordinated, possibly allowing water to enter the coordination sphere of the lanthanide. The washed polymer was tested for its ability to rebind PMT by exposing it to a 150 ppm PMP solution in aqueous IM NaOH and obtaining its luminescence spectra. The 610 nm peak was observed in the spectra.

Example 4

Fiber Optic Sensor

A fiber optic sensor comprising a 400 micron optical fiber (Thor Labs, Newton, N.J., 07860) with the polymeric sensing element chemically bound on its distal end was constructed. The fibers were prepared by terminating one end with an SMA connector and removing the cladding from and polishing the distal end using the procedures outlined in the "Thor Labs Guide to Connectorization and Polishing of Optical Fibers". The tips were dipped into the chemically initiated viscous copolymer described in Example 2 leaving a uniform layer on the fiber. The polymer finished curing under a small UV lamp, overnight. Coated fibers were conditioned in a manner similar to the ground polymers as outlined above. Final versions of the sensor were prepared using a tapered fiber created by heating it in an air/acetylene flame and manually pulling the stripped end. The tapered fibers were much more efficient at coupling the evanescent field to the polymer and gave greatly improved results.

Figure 7:
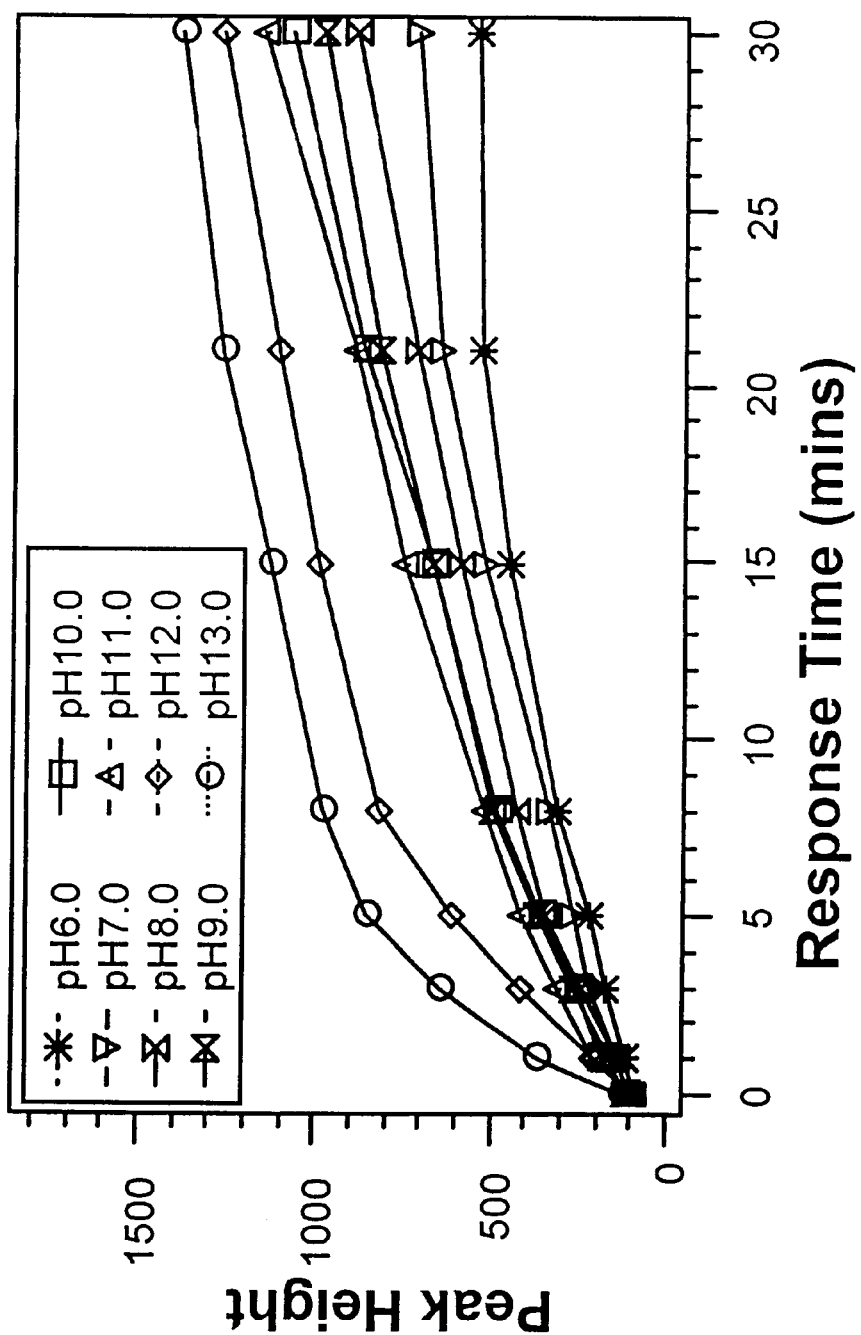
FIG. 7 shows the effect of pH on the temporal response of an optic sensor of the present invention.

Differing thicknesses of the polymeric coating were used to evaluate the effects of polymer thickness on response time, background signal and signal intensity. Thickness was controlled by the number of times the fiber was dipped into the viscous polymer. Digital images of the coated and uncoated fibers were taken using a scanning electron microscope (SEM). The fibers were analyzed at low acceleration voltages with no prior sample preparation. (Low acceleration voltage was used to minimize charging artifacts on the fibers.) The images were acquired using SM701-AP software available from the vendor. During the imaging, measurements of the polymer thickness were performed (FIG. 7), and the average thickness resulting from each dip was estimated to be between 15 and 20 gm. It was observed that increasing the thickness of the coating undesirably increased the time required for response and the intensity of a residual 610 nn peak in the background. This is consistent with the fact that thicker coatings have cavities that are deeper in the polymer and are relatively inaccessible. Thus, a larger amount of PMP could remain trapped in the polymer increasing the residual peak. A thickness of four coats, approximately 60 to 80 gm was determined to be optimal for the design of the sensors since it gives an 80% response within a reasonable time (less than 8 minutes).

Example 5

Analysis

Measurements for the calibration data, pH study, and interference testing of the sensor described in Example 3 were all performed using the same fiber. The analytical figures of merit were obtained using serial dilutions of a 100 ppm PMP standard in 0.01 M NaOH.

Luminescence was excited using the argon laser and the active end of the sensor was placed in a quartz cuvette containing one of the sample dilutions. Two argon ion excitation wavelengths 465.8 and 488 nm, were used with the polymer. The spectrum of the sensor excited with the 465.8 nm laser line displayed better spectral resolution of the 610 nm analyte peak from the 615 rim luminescence peak of the parent europium. The luminescence of the compound excited at 465.8 nm was also more intense. This increase indicates that excitation using the 465.8 nm line results in a near resonant excitation transition from the ground 7Fo level to the SD2 level. As a result, 465.8 run was chosen as the excitation wavelength for the sensor. Spectra were collected at each concentration after the sensor had equilibrated for 10 minutes. The sensor was rinsed with deionized water between each concentration. Standards were analyzed in order of both increasing and decreasing concentration in order to demonstrate the reversibility of the sensor. Calibration curves were obtained and linear regressions were performed.

The response of the sensor and the pH dependence of the temporal response were evaluated. A series of 100 ppm pinacolylmethylphosphonate standards with pH values ranging from 4.5 to 13.0 were prepared from the stock standard through the addition of 1.0M nitric acid or 1.0 M sodium hydroxide. The sensor was placed in a cuvette with each solution and spectra collected at a variety of exposure times. Response was evaluated through a comparison of peak intensity at each time with pH.

A series of pesticide and insecticide standards along with a phosphate buffer solution were tested as possible interference. Standard 1000 ppm solutions were prepared by the dissolution and/or dilution of the samples in deionized water when possible. The pesticides with limited solubility in water were prepared using a 50:50 water/methanol mixture. The pH of each of the solutions was adjusted to 12 using 1 M sodium hydroxide. Spectra from the fiber for each analyte were taken at regular intervals for 60 minutes. The resulting spectra were then compared with the response from the sensor in 100 ppm PMP. The sensor was cleaned using 1 M nitric acid and rinsed with deionized water between each analysis.

Figure 8:
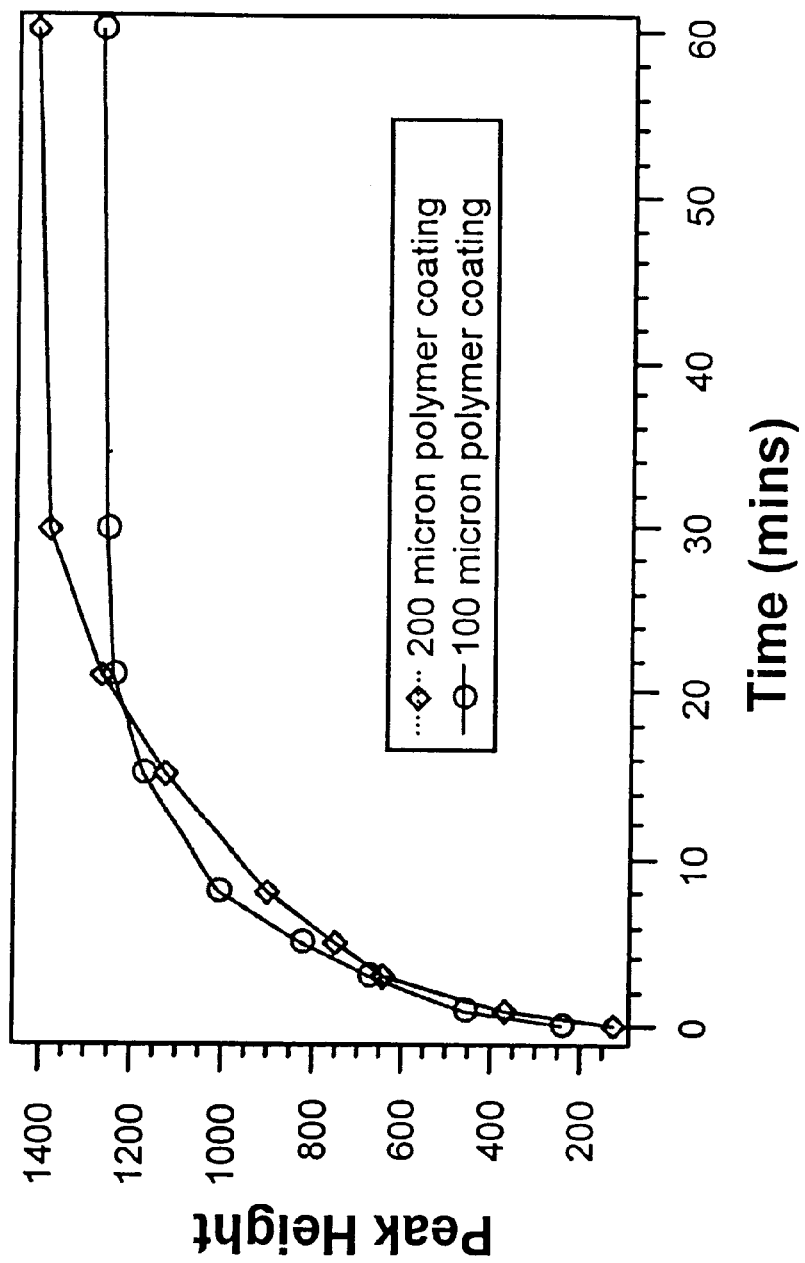
FIG. 8 shows the effect of the thickness of the polymer coating on temporal response.

$Eu(DMMB)_3PMP(NO^-)_2$ demonstrated a relatively easily discernible spectral difference. See FIG. 8. The luminescence intensity of this compound was not as large as some of the other candidates, however, the clarity of the spectral difference between the compound with and without the hydrolysis product made detection based on the spectrum a relatively simple process. In order to verify that the new peak was not simply a result of a mixture of Eu(PMP)$_3$ and the complex, Eu(PMP)$_3$ was prepared and its luminescence spectrum generated. The peak at 610 nm in the $^7F_2 \leftarrow {}^5D_o$ manifold of Eu3+ for the compound was clearly not in the spectrum of Eu(PMP)$_3$. The Eu(PMP)$_3$ displayed weak luminescence and poor resolution. The Eu(PMP)$_3$ spectra strongly suggests that the peak at 610 nm was due to the addition of the hydrolysis product to the compound and not an impurity.

Low temperature (77K) luminescence spectra were analyzed using 465.8 nm excitation to determine the site symmetry of the europium in the compounds. Changes in the spectra were used to elucidate the effects of the substitution of PMP for nitrate. Structural inferences were based on the splitting patterns observed in the $^7F_n \leftarrow {}^5D_o$ (where n=0 to 5) manifolds of the europium spectrum. Stump, N. A., et al., *Spectroscopy Letters* 28:1421 (1992).

Lifetime determinations were performed on the DMMB compounds. Using weighted regression, the lifetimes for Eu(DVMB)3PMP(NO$_3$)$_2$ and Eu(DVMB)$_3$(NO$_3$)$_3$ were calculated to be 337.6 microsec and 312.5 microsec, respectively. Quantum efficiencies for the compounds were determined using a europium perchlorate compound of known quantum efficiency, 1.9%. The determination was based on the ratios of the peak areas in the 500–800 run region of the spectra of three compounds. The quantum efficiencies with and without PMP were 8.54% and 7.76%, respectively. The molar absorptivities were the same for all the compounds (0.0083 L cm-1 moles). The spectrum of the analogous divinyl compounds were examined and found to produce the same spectra as the dimethyl complex. The position of the 610 nm band of interest remained unaffected by the vinyl substitution.

The performance of the fiber optic sensor with the ¼ meter monochromator was evaluated. The sensor used to determine the limit of detection consisted of a 400 pm optical fiber with a tapered end. A 50–75 gm layer of the 3 mole percent polymer was directly deposited on to the end. The fiber was cleaned using the method previously described. Using 1 mW of 465.8 nm for excitation, 200 μm slits with the monochromator, and an exposure time of 5 seconds, the luminescence spectrum of the sensor in a series of PMP solutions at pH 13, was obtained. The response of the sensor to increasing concentrations of PMT exhibits an increase in the luminescence intensity of the primary europium band as well as an increase in the intensity of the analyte peak. This increase in the luminescence is indicative of the rebinding of the PMP product into the primary coordination sphere of the lanthanide and the exclusion of water. The structural determination performed for the characterization of the compound also supports this conclusion. The resulting peak areas in the 609 to 611 nm spectral region of the analyte were calculated using Igor Pro Software, and plotted as a function of concentration. Peak areas have been shown to provide a longer, more linear calibration curve than direct peak height, since the band widths as well as the peak heights of the lanthanides increase as a function of concentration. Linear regression analysis was performed on the data and a limit of detection of 750 ppq calculated. The analytical figures of merit for the sensor with the benchtop apparatus are given in Table 1. Concentrations below 750 ppq show no change in the intensity of either band. The residual 610 nm band remains visible even when the sensor is cleaned, and should be subtracted out with the background for application purposes. Variations in the residual peak, the background, or other slight differences between sensors appear to have little effect on the overall calibration curve, linear dynamic range and limit of detection. The typical 80% response time for the sensor was less than 8 minutes.

Example 6

Response Time and pH Dependence

Figure 9:
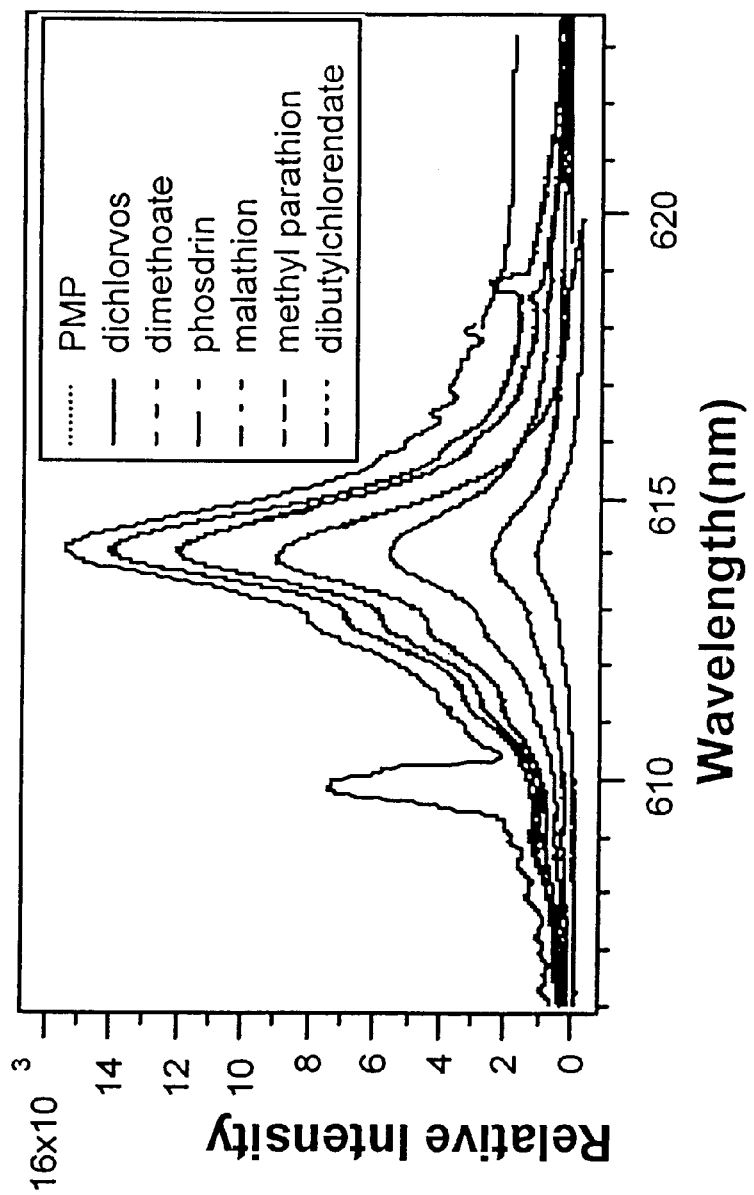
FIG. 9 shows response of an optical sensor of the present invention to selected interferents (pesticides) excited at 465.8 nm.

The response time of the sensor is the most crucial characteristic of detectors and sensors for real-time monitoring. Yang, Y. C., et al., *Chemical Reviews*, 92:1729–1743 (1992). A study was performed using a sensor with a 200 micron coat to determine the effect of pH on the response time and on solutions of PMP prepared with pH values ranging from about 4.5 to 13 over a period of 24 hours. FIG. 9 shows the response of the sensor over the initial 30 minute time period. Additional readings were obtained for each pH value at 1 hour and at 24 hours. (Since these points remained at the same value they were excluded for reasons of clarity.) The sensors show a positive response to the presence of PMP after 3 minutes for all pH values from 6 to 12, and a positive response after 1 minute for the solution with a pH of 13. At low values of pH (below 6), the response of the sensor is indicative of the removal of PMP from the sensor. This demonstrates the washing process that occurs under acidic conditions. Neutral and slightly basic values (pH from 6–11) provide a response that is consistent over the entire pH range. The full response time for this sensor is 30 minutes. (Response times are typically reported as the time it takes the sensor to reach 80% of maximum.) Report "Assessment of Chemical and Biological Sensor Technologies," National Research Council (1984). The response at pH=12 was faster than the response at lower pH levels and had a steeper, more linear response over the initial range of concentration. At this pH, the capacity response time of the sensor was 15 minutes.

The fastest response time for a sensor with a 200 micron coat was obtained using a PMP solution adjusted to pH of about 13 with NaOH. Using this pH, a capacity response time of 14 minutes was obtained. These results indicate that the more basic the solution, the faster the response time of the sensor. Since the response of the sensor will be based on the hydrolysis of the agents, the strongly alkaline solution used for the hydrolysis of the nerve agents will also enhance the response time of the sensor. (All solutions above pH 6 were prepared using deionized water, 1M sodium hydroxide, and PMP.)

Figure 10:
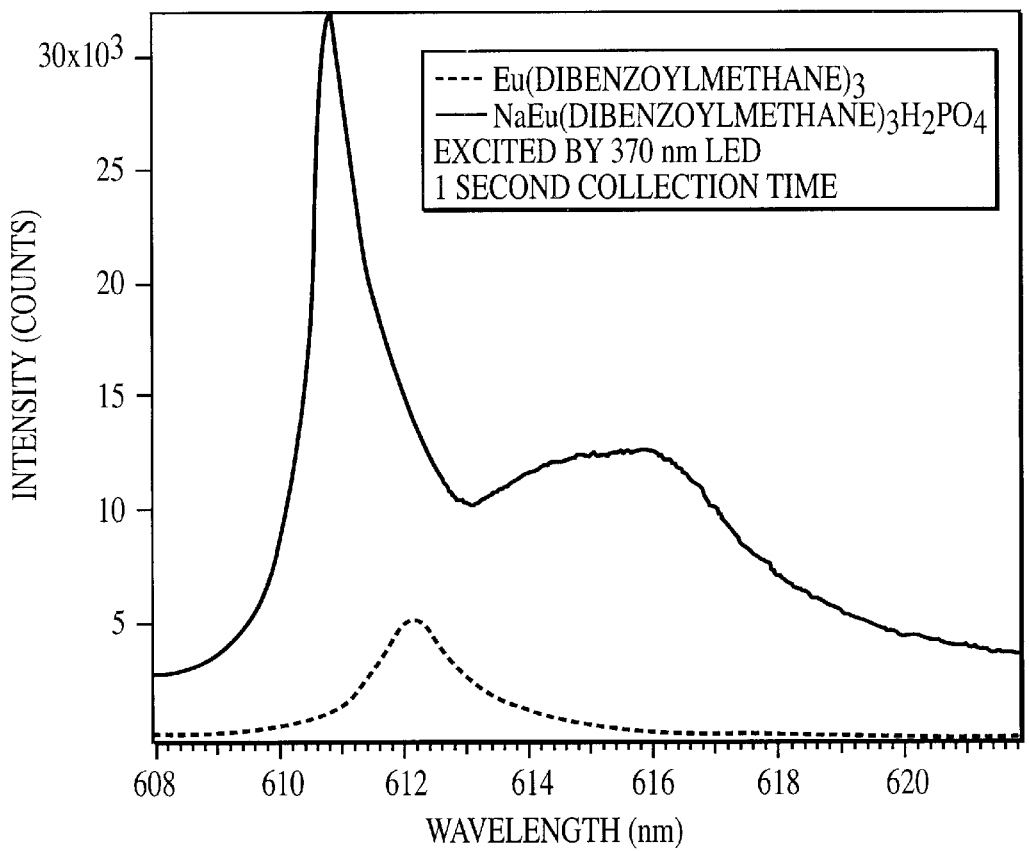
FIG. 10 is LED excited luminescence spectra of $Eu(dibenzoylmethane)_3$ and $NaEu(dibenzoylmethane)_3H_2PO_4$ crystalline solids excited at 370 nm.

The effect of coating thickness on the response time of the sensor was also evaluated. FIG. 10 shows the response of a sensor coated with a 100 micron layer and that of a sensor coated with a 200 micron layer to a 10 ppm PMT solution at pH=13. As previously stated, the fiber with a 200 micron coat reaches a maximum response within 14 minutes. The 80% response time of the 100 micron coated fiber is decreased to 8 minutes. For an on-line monitor, the time for initial response is the most important factor. Using pH=13, a distinct response occurred within 1 minute.

Example 7

Effect of Interferents on Detection

The compounds that are most chemically analogous to nerve agents are organophosphorus pesticides and herbicides. Many of these compounds exist as liquids, oils or solids at ambient temperatures. Several common pesticides, along with those most chemically similar to the agents sarin and soman were tested using the sensor in order to determine the degree of interference from each pesticide. The concentration used for screening 1000 ppm, is much higher than typically found in water systems even with runoff from nearby agriculture. The pesticide dichlorvos, commonly found in flea collars, was also screened as a possible interference.

Each of the pesticides and a sodium phosphate solution was exposed to the sensor prepared in the above Examples for an hour with measurements taken during scheduled intervals. None of the pesticides produced a luminescence peak in the region of the PMP peak. The spectra resulting from the exposure of selected pesticides (concentration 1000 ppm) with the sensor are shown in FIG. 11. The spectrum of the sensor with 100 ppm of the hydrolysis product is shown for comparison purposes. The influence of these chemicals is apparent as indicated by the changing intensity of the major 617 run europium luminescence band. Dichlorvos, the pesticide most structurally similar to the nerve agents, exhibited a response to the sensor with a weak band centered at 621.5 nm. This resulting band does not inhibit the acquisition or detection of the agents by the sensor. Since the chemicals that are the most likely interferences do not cause false positive readings, other less similar compounds should be unlikely to interfere. In addition, none of the pesticides screened were irreversibly bound to the sensor so poisoning is not a concern.

Example 8

Miniaturization

The device based on an Ocean Optics spectrometer exhibited favorable sensitivity and selectivity in detecting the agents on a smaller scale. Using the miniature spectrometer, the entire instrument fits on a board 3.5'×2.5'. The limit of detection for this device was determined using the same procedure used to determine the limit of detection for the larger system. This system provides a limit of detection of 7 parts per trillion using approximately, 1 mW of 465.8 nm laser power and an integration time of 500 microseconds. The linear dynamic range of the device is from 7 ppt to 1 ppm using a 75 p.m coating of fiber. Although the thinner coating limits the number of sites available for rebinding thereby limiting the upper end of the dynamic range, it provides a faster response time for the sensor, on the order of 1 minute at a pH of 12. Three averages were used for the determination of detection limit. Signal averaging and smoothing using the SavitzskyGoulay method was kept to a minimal 3 point average to get the required resolution. Figures of merit for this device are presented in Table 1.

TABLE 1

Comparison of the Analytical Figures of Merit for the Two Systems

| | Lab Bench System | Portable System |
| --- | --- | --- |
| Limit of Detection | 660 ppq | 7 ppt |
| Linear Dynamic Range | 750 ppq to 10 ppm | 10 ppt to 10 ppm |
| Correlation Coefficient (r2) | 0.9984 | 0.9973 |
| Slope | 1.949 counts ppt-1 | 1.484 p.V ppt-I |
| 80% Response Time | 8 minutes | 8 minutes |

Although specific features of the invention are shown in some drawings and not others, this is for convenience only as each feature may be combined with any or all of the other features in accordance with the invention. It will be appreciated that variations thereof can be readily perceived by those skilled in the art, which variations are nevertheless within the scope of the invention as defined by the following claims.

What is claimed is:

1. A sensor device for detecting an analyte comprising a molecularly imprinted polymer containing a chelated lanthanide, said chelated lanthanide comprising a lanthanide ion wherein said lanthanide ion is a europium or terbium ion, wherein the lanthanide ion is chelated with the polymerized derivate(s) of one or more ligands selected from the group consisting of vinyldibenzoylmethane, divinyldibenzoylmethane, vinyl-substituted 1,10-phenanthroline, and mixtures of two or more thereof, said chelated lanthanide capable of binding the analyte to be detected and having operatively associated therewith:
 a light source for generating excitation energy for said chelated lanthanide; and
 a detector for detecting luminescent energy generated by said chelated lanthanide upon excitation.

2. The sensor device of claim 1 wherein the light source is selected from the group consisting of an argon laser, blue laser, tunable laser, light emitting diode, and combinations of two or more thereof.

3. The sensor device of claim 2 wherein the light source is a light emitting diode.

4. The sensor device of claim 1 wherein the detector is selected from the group consisting of a spectrophotometer, spectrometer, photomultiplier tube, monochromator equipped with a CCD camera, filters, the naked eye, and combinations of two or more thereof.

5. The sensor device of claim 1 further comprising at least one optical fiber, having a proximal end and a distal end, for transmitting light energy, wherein said molecularly imprinted polymer is disposed onto distal end of the optical fiber, said light source is operatively associated with said optical fiber such that said fiber is capable of transmitting excitation energy generated by the light source to said molecularly imprinted polymer, and said detector is operatively associated with said optical fiber such that said detector is capable of detecting luminescence from said chelated lanthanide.

6. A sensor device for detecting an analyte comprising a molecularly imprinted polymer containing a chelated lanthanide, said chelated lanthanide comprising a lanthanide ion wherein said lanthanide ion is a +3 europium ion, wherein the lanthanide ion is chelated with the polymerized derivate(s) of one or more ligands selected from the group consisting of vinyldibenzoylmethane, divinyldibenzoylmethane, vinyl-substituted 1,10-phenanthroline, and mixtures of two or more thereof, said chelated lanthanide capable of binding the analyte to be detected and having operatively associated therewith:
 a light source for generating excitation energy for said chelated lanthanide;
 a detector for detecting luminescent energy generated by said chelated lanthanide upon excitation; and
 at least one optical fiber, having a proximal end and a distal end, for transmitting light energy, wherein said molecularly imprinted polymer is disposed on the distal end of the optical fiber, said light source is operatively associated with said optical fiber such that said fiber is capable of transmitting excitation energy generated by the light source to said molecularly imprinted polymer, and said detector is operatively associated with said optical fiber such that said detector is capable of detecting luminescence from said chelated lanthanide.

7. The sensor device of claim 6 wherein the light source is a light emitting diode.

8. The sensor device of claim 7 wherein the detector is selected from the group consisting of a spectrophotometer, spectrometer, photomultiplier tube, monochromator equipped with a CCD camera, filters, the naked eye, and combinations of two or more thereof.

9. A method for detecting a target analyte comprising providing a solution comprising an analyte to be detected and contacting said solution with the molecularly imprinted polymer of a sensor device of claims 1 or 6.

10. The method of claim 9 wherein said analyte is bound to a chelated lanthanide in said molecularly imprinted polymer.

11. The method of claim 10 wherein at least a portion of said molecularly imprinted polymer of said device is immersed within said solution.

12. A method of making a molecularly imprinted polymer comprising:

mixing a lanthanide salt with one or more polymerizable lanthanide-coordinating ligand compounds and a polyatomic anion target analyte imprint molecule under conditions effective to produce a chelated lanthanide-analyte complex;

co-polymerizing the lanthanide-analyte complex with one or more cross-linking monomers, and one or more matrix monomers to form a polymer structure; and removing the imprint molecule from the polymer structure to form an MIP.

13. The method of claim 12 wherein said lanthanide salt is a salt of a lanthanide selected from the group consisting of lanthanum, cerium, praseodymium, neodymium, promethium, samarium, europium, gadolinium, terbium, dysprosium, holmium, erbium, thulium, ytterbium, and lutetium.

14. The method of claim 13 wherein said polymerizable ligand compounds are selected from the group consisting of 4-vinyl benzoic acid, methyl-3,5-divinyl benzoate, 4-vinyl-2-hydroxybenzaldehyde oxime, 2-hydroxy-1,2-di-4-vinylphenylethanone (benzoin oxime vinyl derivative), vinyldibenzoylmethane, divinyldibenzoylmethane, vinyl-substituted 1,10-phenanthroline, and mixtures of two or more thereof.

15. The method of claim 14 wherein said polyatomic anion is selected from the group consisting of nitrate, perchlorate, and phosphates.

16. The method of claim 12 wherein said matrix monomer is selected from the group consisting of divinyl benzene, styrene, and azobisisobutylnitrile.

* * * * *